United States Patent
Schaeffer et al.

(10) Patent No.: US 9,326,871 B2
(45) Date of Patent: *May 3, 2016

(54) INTRALUMENALLY-IMPLANTABLE FRAMES

(71) Applicant: Cook Medical Technologies LLC, Bloomington, IN (US)

(72) Inventors: Darin G. Schaeffer, Bloomington, IN (US); Jacob A. Flagle, Indianapolis, IN (US); Michael L. Garrison, Indianapolis, IN (US); Brian C. Case, Lake Villa, IL (US); Andrew K. Hoffa, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 147 days.

This patent is subject to a terminal disclaimer.

(21) Appl. No.: 14/324,435

(22) Filed: Jul. 7, 2014

(65) Prior Publication Data

US 2014/0379070 A1 Dec. 25, 2014

Related U.S. Application Data

(63) Continuation of application No. 13/924,830, filed on Jun. 24, 2013, now Pat. No. 8,771,338, which is a continuation of application No. 13/447,619, filed on Apr. 16, 2012, now Pat. No. 8,470,020, which is a (Continued)

(51) Int. Cl.
*A61F 2/06* (2013.01)
*A61F 2/24* (2006.01)

(Continued)

(52) U.S. Cl.
CPC ... *A61F 2/86* (2013.01); *A61F 2/06* (2013.01); *A61F 2/2418* (2013.01);
(Continued)

(58) Field of Classification Search
CPC ........... A61F 2/90; A61F 2/91; A61F 2/2418; A61F 2/2412; A61F 2/86
See application file for complete search history.

(56) References Cited

U.S. PATENT DOCUMENTS

| 2,832,078 A | 4/1958 | Williams |
| 3,657,744 A | 4/1972 | Ersek |

(Continued)

FOREIGN PATENT DOCUMENTS

| EP | 0850607 | 7/1998 |
| JP | S62-227352 | 8/1994 |

(Continued)

OTHER PUBLICATIONS

European Search Report and Search Opinion, issued by the European Patent Office, Nov. 9, 2009 for Application No. 09170581.4-2320.

(Continued)

*Primary Examiner* — Jason-Dennis Stewart
(74) *Attorney, Agent, or Firm* — Buchanan Nipper

(57) ABSTRACT

Implantable frames for use in body passages are provided herein. The implantable frames can include a plurality of hoop members joined by a plurality of longitudinal connecting members to form a tubular frame defining a cylindrical lumen. The plurality of longitudinal connecting members may include first and second longitudinal connecting members joining a first hoop member to a second hoop member such that the first and second longitudinal connecting members extend across an entire space separating the first and second hoop members.

20 Claims, 11 Drawing Sheets

Related U.S. Application Data continuation of application No. 12/605,585, filed on Oct. 26, 2009, now Pat. No. 8,157,857, which is a continuation of application No. 11/545,746, filed on Oct. 10, 2006, now Pat. No. 7,625,399, which is a continuation-in-part of application No. 10/828,716, filed on Aug. 30, 2004, now Pat. No. 7,618,447, said application No. 11/545,746 is a continuation-in-part of application No. 11/487,629, filed on Jul. 17, 2006, now Pat. No. 7,658,759.

(60) Provisional application No. 60/465,141, filed on Apr. 24, 2003, provisional application No. 60/530,781, filed on Dec. 18, 2003, provisional application No. 60/700,852, filed on Jul. 19, 2005, provisional application No. 60/725,678, filed on Oct. 12, 2005.

(51) Int. Cl.
*A61F 2/86* (2013.01)
*A61F 2/915* (2013.01)
*A61F 2/91* (2013.01)

(52) U.S. Cl.
CPC .............. *A61F 2/2475* (2013.01); *A61F 2/915* (2013.01); *A61F 2/91* (2013.01); *A61F 2002/068* (2013.01); *A61F 2002/91508* (2013.01); *A61F 2002/91516* (2013.01); *A61F 2002/91533* (2013.01); *A61F 2002/91575* (2013.01); *A61F 2220/0016* (2013.01); *A61F 2220/0058* (2013.01); *A61F 2230/0054* (2013.01); *A61F 2250/0037* (2013.01); *A61F 2250/0039* (2013.01)

(56) References Cited

U.S. PATENT DOCUMENTS

| | | | |
|---|---|---|---|
| 4,297,749 | A | 11/1981 | Davis et al. |
| 4,441,216 | A | 4/1984 | Ionescu et al. |
| 5,411,552 | A | 5/1995 | Andersen et al. |
| 5,545,215 | A | 8/1996 | Duran |
| 5,607,465 | A | 3/1997 | Camilli |
| 5,709,707 | A | 1/1998 | Lock et al. |
| 5,713,953 | A | 2/1998 | Vallana et al. |
| 5,733,325 | A | 3/1998 | Robinson et al. |
| 5,824,042 | A | 10/1998 | Lombardi et al. |
| 5,840,081 | A | 11/1998 | Anderson et al. |
| 5,855,601 | A | 1/1999 | Bessler et al. |
| 5,879,382 | A | 3/1999 | Boneau |
| 5,907,893 | A | 6/1999 | Zadno-Azizi et al. |
| 5,957,949 | A | 9/1999 | Leonhardt et al. |
| 6,099,561 | A | 8/2000 | Alt |
| 6,280,467 | B1 | 8/2001 | Leonhardt |
| 6,287,334 | B1 | 9/2001 | Moll et al. |
| 6,299,637 | B1 | 10/2001 | Shaolian et al. |
| 6,338,730 | B1 | 1/2002 | Bonutti et al. |
| 6,458,153 | B1 | 10/2002 | Bailey et al. |
| 6,494,909 | B2 | 12/2002 | Greenhalgh |
| 6,596,021 | B1 | 7/2003 | Lootz |
| 6,669,724 | B2 | 12/2003 | Park et al. |
| 6,676,698 | B2 | 1/2004 | McGuckin, Jr. et al. |
| 7,044,966 | B2 | 5/2006 | Svanidze et al. |
| 7,101,396 | B2 | 9/2006 | Artof et al. |
| 7,128,759 | B2 | 10/2006 | Osborne et al. |
| 7,147,661 | B2 | 12/2006 | Chobotov et al. |
| 7,195,641 | B2 | 3/2007 | Palmaz et al. |
| 7,347,869 | B2 | 3/2008 | Hojeibane et al. |
| 7,351,256 | B2 | 4/2008 | Hojeibane et al. |
| 7,354,455 | B2 | 4/2008 | Stinson |
| 7,377,938 | B2 | 5/2008 | Sarac et al. |
| 7,381,219 | B2 | 6/2008 | Salahieh et al. |
| 7,445,631 | B2 | 11/2008 | Salahieh et al. |
| 7,452,371 | B2 | 11/2008 | Pavcnik et al. |
| 7,524,331 | B2 | 4/2009 | Birdsall |
| 7,544,207 | B2 | 6/2009 | Osborne et al. |
| 8,157,857 | B2 | 4/2012 | Case et al. |
| 8,771,338 | B2 | 7/2014 | Schaeffer et al. |
| 2001/0018610 | A1 | 8/2001 | Limon |
| 2001/0039450 | A1 | 11/2001 | Pavcnik et al. |
| 2002/0193871 | A1 | 12/2002 | Beyersdorf et al. |
| 2003/0109922 | A1 | 6/2003 | Peterson et al. |
| 2003/0114919 | A1 | 6/2003 | McQuiston et al. |
| 2003/0236568 | A1 | 12/2003 | Hojeibane et al. |
| 2004/0019374 | A1 | 1/2004 | Hojeibane et al. |
| 2004/0093070 | A1 | 5/2004 | Hojeibane et al. |
| 2004/0260389 | A1 | 12/2004 | Case et al. |
| 2005/0059923 | A1 | 3/2005 | Gamboa |
| 2005/0075713 | A1 | 4/2005 | Biancucci et al. |
| 2005/0096735 | A1 | 5/2005 | Hojeibane et al. |
| 2007/0038291 | A1 | 2/2007 | Case et al. |
| 2007/0260327 | A1 | 11/2007 | Case et al. |
| 2013/0289706 | A1 | 10/2013 | Schaeffer et al. |

FOREIGN PATENT DOCUMENTS

| | | |
|---|---|---|
| WO | 8302225 | 7/1983 |
| WO | 0154625 | 8/2001 |
| WO | WO0236048 | 5/2002 |
| WO | WO03003949 | 1/2003 |
| WO | 03030776 | 4/2003 |

OTHER PUBLICATIONS

U.S. Appl. No. 12/614,878, Final Office Action mailed on Dec. 27, 2010.

European Patent Office, "Extended European Search Report," for application No. 14183091.9, mailed on Jun. 15, 2015, pp. 1-6.

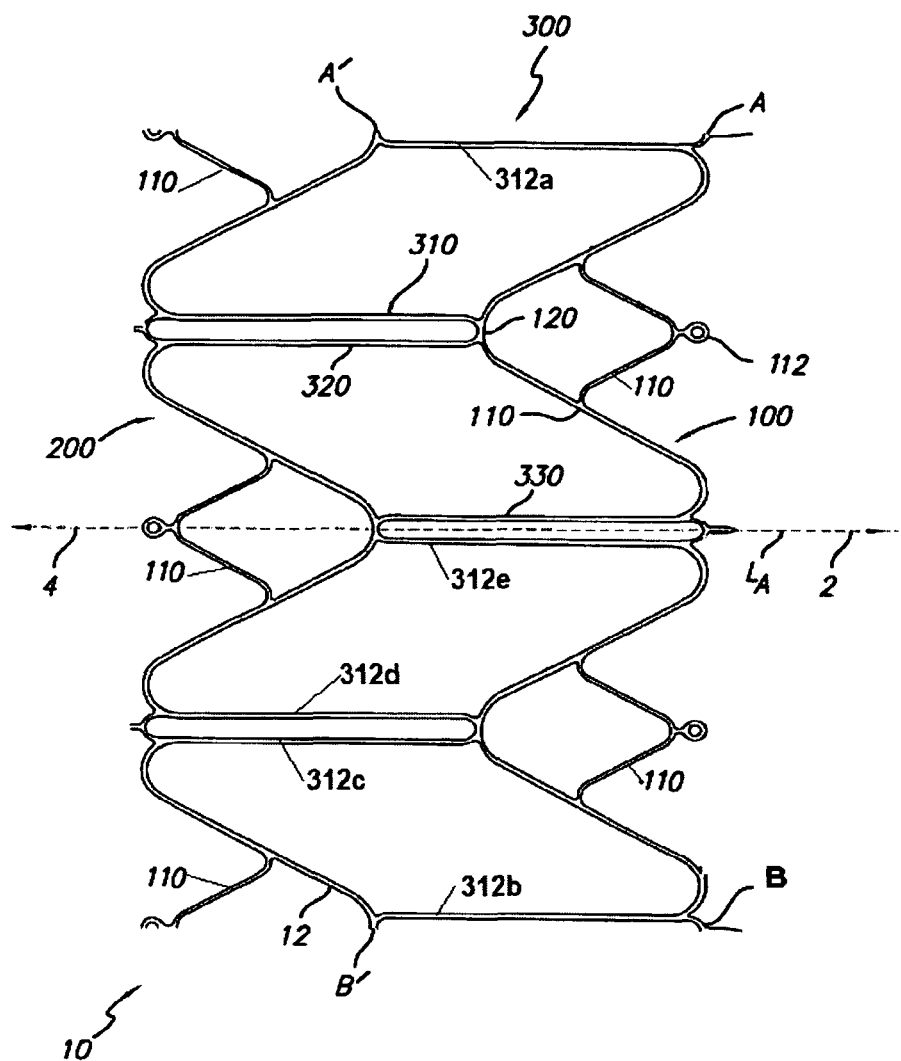

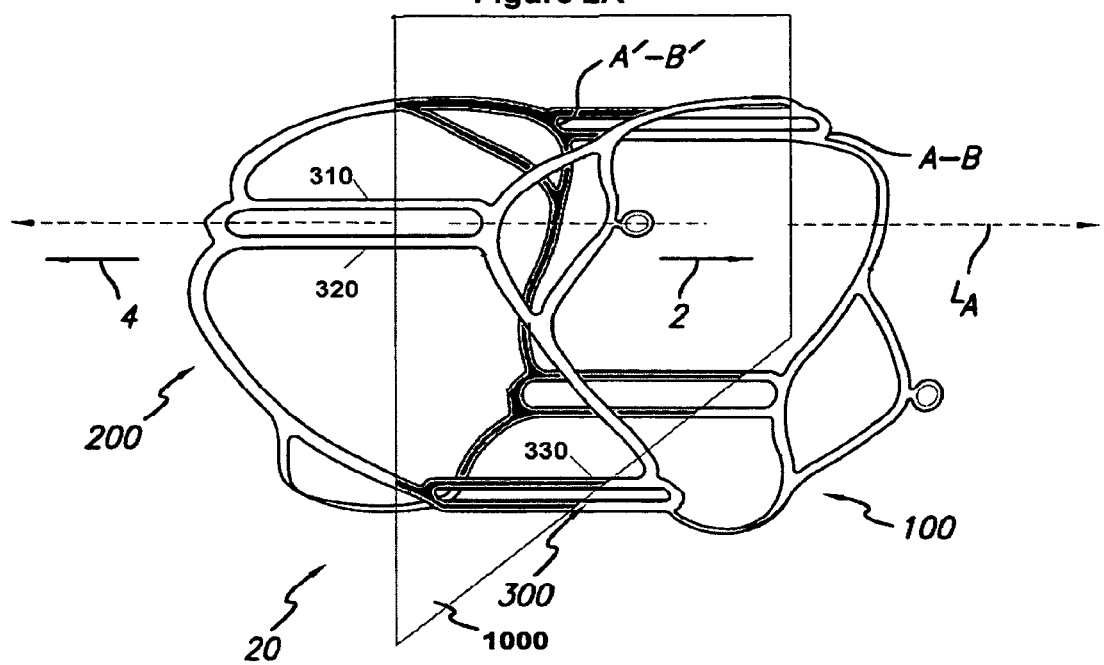

INTRALUMENALLY-IMPLANTABLE FRAMES

RELATED APPLICATIONS

This application is a continuation of co-pending U.S. patent application Ser. No. 13/924,830, filed on Jun. 24, 2013, which is a continuation of application Ser. No. 13/447,619, filed on Apr. 16, 2012, which is a continuation of U.S. patent application Ser. No. 12/605,585, filed on Oct. 26, 2009, and now U.S. Pat. No. 8,157,857, which is a continuation of U.S. patent application Ser. No. 11/545,746, filed on Oct. 10, 2006, and now U.S. Pat. No. 7,625,399, which claims the benefit of U.S. provisional patent application 60/725,678, filed Oct. 12, 2005; and which is a continuation-in-part of U.S. patent application Ser. No. 10/828,716, filed Aug. 30, 2004, and now U.S. Pat. No. 7,618,447, which in turn claims priority to U.S. provisional applications 60/465,141 filed Apr. 24, 2003, and 60/530,781, filed Dec. 18, 2003; and which is also a continuation-in-part of U.S. patent application Ser. No. 11/487,629, filed Jul. 17, 2006, and now U.S. Pat. No. 7,658,759, which in turn claims the benefit of U.S. provisional patent application 60/700,852, filed Jul. 19, 2005. Each of these related applications is incorporated into this disclosure in its entirety.

TECHNICAL FIELD

The present invention relates generally to the field of intralumenally-implantable medical device frames for placement in a body passage and related methods of treatment. The implantable frames can be used as stents, or form portions of valves or stent grafts.

BACKGROUND

Intralumenally implantable frames can be implanted to treat a variety of medical conditions. Implantable frames can maintain patency of body vessels or provide support for a valve or valve leaflets for regulating fluid flow within a body lumen. For example, flexible leaflet material can be attached to an implantable frame to form a valve prosthesis useful in providing an artificial valve for treating venous valve insufficiency. In addition, a variety of other implantable prostheses, such as stents, stent grafts and the like, comprise a radially expandable support frame placed within the body to improve the function of a body lumen. Support frames may be implanted in vessels, ducts or channels of the human body and can form part of a valve to regulate fluid flow within a body lumen or as scaffolding to maintain the patency of a body vessel, duct or channel to treat various conditions.

Endolumenal prostheses comprising support frames can be placed in a body lumen from a delivery system which includes a catheter. Implantable frames can be intralumenally delivered inside the body by a catheter that supports the stent in a radially compressed form as it is transported to a desired site in a body vessel. Upon reaching the site, the implantable frame can be radially expanded and securably positioned within the lumen of the body vessel, for example by engaging the walls of the body vessel with a portion of the implantable frame. The expansion mechanism may involve expanding the implantable frame radially outward, for example by inflation of a balloon carried by the catheter. Alternatively, when the implantable frame is formed of a self-expanding material, the implantable frame may be delivered in a radially restrained configuration and deployed by removing the restraint at a point of treatment to allow the implantable frame to self-expand by its own internal elastic restoring force at a point of treatment. After expansion of the implantable frame, the catheter delivery system is subsequently withdrawn from the body vessel. Endolumenally implantable support frames preferably possess sufficient hoop strength to resist collapse of the body vessel, while maintaining a desired degree of radial or longitudinal flexibility to prevent damage to the body vessel.

Implantable frames are subjected to various mechanical forces before, during and after deployment within a body lumen. Before deployment, implantable frames can be compressed and maintained in a compacted form, which can include subjecting the implantable frame to a prolonged inward radial restraining force. During deployment, implantable frames can be subjected to an outward radial expanding force, for example from a balloon expansion or self-expansion process. The implantable frames can also be subjected to an inward radial compressive force upon contact with the body vessel wall during deployment expansion. After deployment, implanted frames can be subject to continued inward radial force from the body vessel wall, in addition to a variety of shearing or tortional forces imparted by movement of the body vessel wall or fluid flow within the body vessel. Uneven mechanical load bearing within an implantable frame can result in uneven wear and distortion of the implantable frame shape, or even failure of structural integrity. In typical sinusoidal and near sinusoidal designs, the bends or radial arcs experience areas of high strain and stress, which can lead to areas of frame fatigue or fracture. However, the stress and/or strain experienced along the length of the radial arc may not be uniform, and there are areas of relatively high stress and/or strain. Therefore, it is desirable to provide implantable frames that more evenly distribute mechanical loads.

Dynamic fluctuations in the shape of the lumen of a body vessel, such as a vein, pose challenges to the design of support frames for implantation within the body vessel. For instance, the flow velocity and diameter of veins do not remain essentially constant at a given systemic vascular resistance. Instead, the shape of vein lumens can fluctuate dynamically in response to the respiration, body position, central venous pressure, arterial inflow and calf muscle pump action of a mammalian subject. The veins also provide the principal volume capacitance organ. For example, an increase of almost 100% in the diameter of the common femoral vein has been observed in human patients simply by rotation of the patient by about 40 degrees, corresponding to a four-fold increase in blood flow volume. Moneta et al., "Duplex ultrasound assessment of venous diameters, peak velocities and flow patterns," J. Vasc. Surg. 8; 286-291 (1988). The shape of a lumen of a vein can undergo dramatic dynamic change as a result of varying blood flow velocities and volumes therethrough, presenting challenges for designing implantable intralumenal prosthetic devices that are compliant to the changing shape of the vein lumen.

Preferably, implantable frames are also configured to minimize undesirable irritation of the lining of a body vessel upon implantation, for example by minimizing the surface area of the frame in contact with the body vessel. However, reducing the surface area of the frame may increase the mechanical stress and strain on particular portions of the frame, particularly bends or arcuate sections. What is needed are endolumenally implantable medical device frames configured to withstand radial compression upon implantation by desirably distributing the associated mechanical strain on the implanted frame, while also minimizing potential irritation of a body vessel that may result from contact between the body vessel and the external surface of the implanted frame.

SUMMARY

Intralumenally implantable frame configurations adapted for placement within a body passage are provided herein. The present disclosure provides implantable frames configured to balance often competing concerns of minimizing potentially irritating external surface area, minimizing foreshortening during radial expansion, and providing a desirable distribution of mechanical loading within the frame during movement of the frame within a dynamic body vessel such as a vein. These implantable frames are particularly useful, for example, as a support for a valve for correcting fluid flow within a body passage, or for opening, dilating and maintaining body vessels and other biological ducts which are at risk of closure or constriction. For example, the implantable frames may be configured as stents for maintaining the patency of a body vessel or as support frames for valves or stent grafts.

The implantable frames preferably have a substantially tubular configuration and include two or more hoop members axially aligned around a longitudinal axis and joined by a plurality of longitudinal connecting members. The hoop members and the longitudinal connecting members define a plurality of open spaces in the exterior surface of the tubular frame. The longitudinal connecting members are preferably arranged in a configuration suitable to provide an implantable frame with a desired radial compression upon implantation while favorably distributing the mechanical strain imparted to the implanted frame due to post-implantation radial compression of the body vessel at the site of implantation. The implantable frames may be configured to minimize potential irritation of a body vessel that may result from contact between the body vessel and the external surface of the implanted frame, for example by minimizing the surface area and number of hoop members and longitudinal connecting members. The implantable frame is preferably adapted for translumenal percutaneous delivery in a radially compressed state from a delivery system comprising a catheter. The frame is preferably moveable between a radially compressed state and a radially expanded state by any suitable means within a body vessel, including balloon expansion or self-expansion from a delivery catheter positioned within a body vessel.

Preferably, the implantable frame comprises a plurality of longitudinal connecting members connecting a pair of hoop members to form a tubular frame defining a cylindrical lumen. The plurality of longitudinal connecting members desirably includes one or more pairs of closely-spaced longitudinal connecting members oriented substantially parallel to the longitudinal axis of the tubular implantable frame. Preferably, a tubular implantable frame includes two or more hoop members axially aligned around a longitudinal axis of the frame. The longitudinal connecting members are preferably substantially straight struts aligned substantially parallel to the longitudinal axis of the implantable frame. In one aspect, the longitudinal connecting members are substantially equal in length.

Longitudinally adjacent hoop members are desirably connected by any suitable number (n) of longitudinal connecting members, where (n) is preferably an integer equal to 2-16, and more preferably 4-8. Preferably, the circumferential distance between longitudinal members varies as a function of the number of longitudinal connecting members, with at least two of the longitudinal connecting members being closely-spaced. Closely-spaced longitudinal connecting members are circumferentially adjacent members that are circumferentially closer to one another than to the next nearest circumferentially adjacent longitudinal connecting member. The circumferential distance between longitudinal connecting members is measured along the outer surface of a transverse cross section of the frame, where the cross section is centered on, and oriented perpendicular to, the longitudinal axis. For example, in a frame having a second longitudinal connecting member circumferentially adjacent to both a first longitudinal connecting member (in a first circumferential direction) and a third longitudinal connecting member (in a circumferential direction opposite the first circumferential direction), the circumferential distance measured between the first longitudinal connecting member and the second longitudinal connecting member that is closely spaced with respect to the first longitudinal connecting member is less than the circumferential distance measured from the first longitudinal connecting member to a third longitudinal connecting member that is not closely-spaced with respect to the first longitudinal connecting member. In one aspect, the angle subtended by a hypothetical arc extending circumferentially along the perimeter of a cross section of a frame from a first longitudinal connecting member to a second longitudinal connecting member that is closely-spaced with respect to the first longitudinal connecting member is less than $(2.\pi./n)$ radians, where (n) is an integer equal to the number of longitudinal connecting members between longitudinally adjacent hoop members. In a second aspect, the shortest circumferential distance between the closely paired longitudinal connecting members can be less than about 25%, preferably less than about 15%, of the length of the closely spaced pair of longitudinal connecting members. The frame desirably includes two or more pairs of closely spaced longitudinal connecting members symmetrically positioned across a tubular frame lumen from another pair of closely spaced longitudinal connecting members.

The hoop members can have any suitable configuration. For example, undulating hoop members typically include a plurality of alternating struts and bends forming a sinusoidal pattern defining a portion of the external surface of a tubular frame. Alternatively, the hoop members can be planar rings formed from a single bent member. Optionally, the frame includes one or more undulating hoop members formed from a plurality of interconnected struts and bends oriented along the longitudinal axis of the frame. For example, a frame can include a first undulating hoop member having a total of (m) struts joined to a total of (2 m) longitudinal connecting members, wherein (m) is preferably an integer equal to 2-16, preferably 2-8. The frame can further comprise a plurality of lateral support arms connecting facing pairs of adjacent struts within the hoop members positioned at the ends of the frame. A lateral support arm preferably comprises a single bend connecting a pair of lateral support struts. The hoop members preferably have substantially similar configurations, although frames may include hoop members with different configurations. The cross section of each hoop member desirably forms a perimeter around a substantially circular or elliptical lumen. Each hoop member can optionally include an undulating pattern of struts and bends extending along the axis of the frame. Preferably, the ratio of bends to struts in an undulating hoop member is 1:1 to 3:1, more preferably 2:1 to 3:1, with the struts having a substantially equal length within each hoop member. Alternatively, one or more hoop members can have a planar geometry, such as a single bent member forming an annular shape. The plurality of hoop members can have the same or different configurations, but are preferably concentrically aligned along the longitudinal axis of the frame. Each of the bends in the hoop members are preferably connected to a longitudinally adjacent hoop member by at least one longitudinal connecting member.

While the invention is defined by the claims appended hereto, additional understanding of the invention can be gained by reference to the attached drawings and the description of preferred embodiments presented below.

BRIEF DESCRIPTION OF THE DRAWINGS

In the accompanying drawings:

FIG. 1A is an unrolled flat plan view of a first implantable frame.

FIG. 2A is a perspective view of the first implantable frame of FIG. 1A shown in the radially expanded configuration, showing a cross sectional plane.

DETAILED DESCRIPTION

Figure 1B:
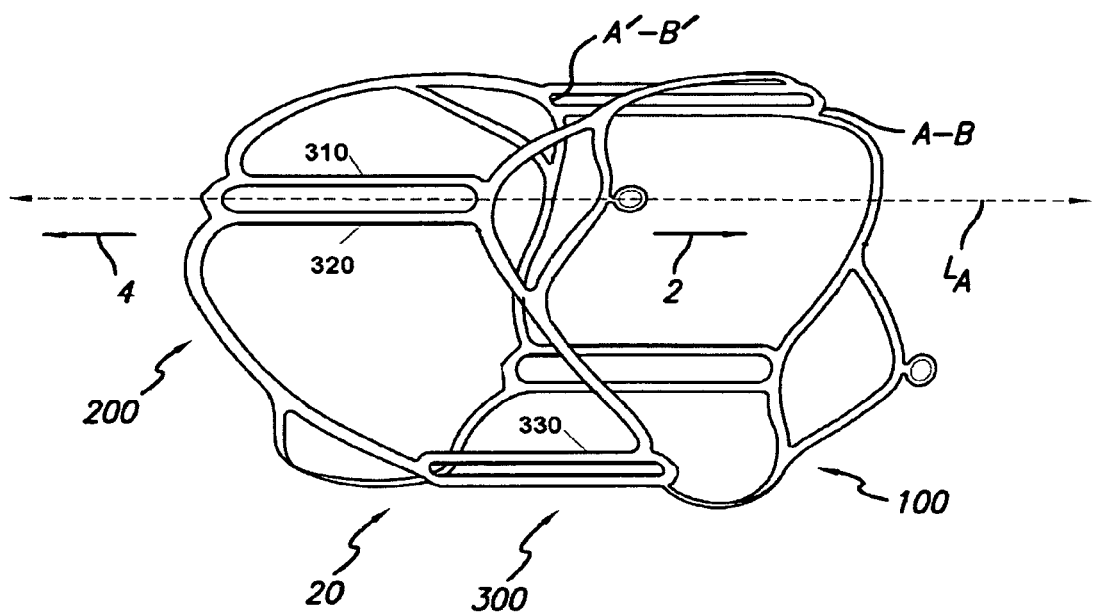
FIG. 1B is a perspective view of the first implantable frame of FIG. 1A shown in the radially expanded configuration.
Figure 1C:
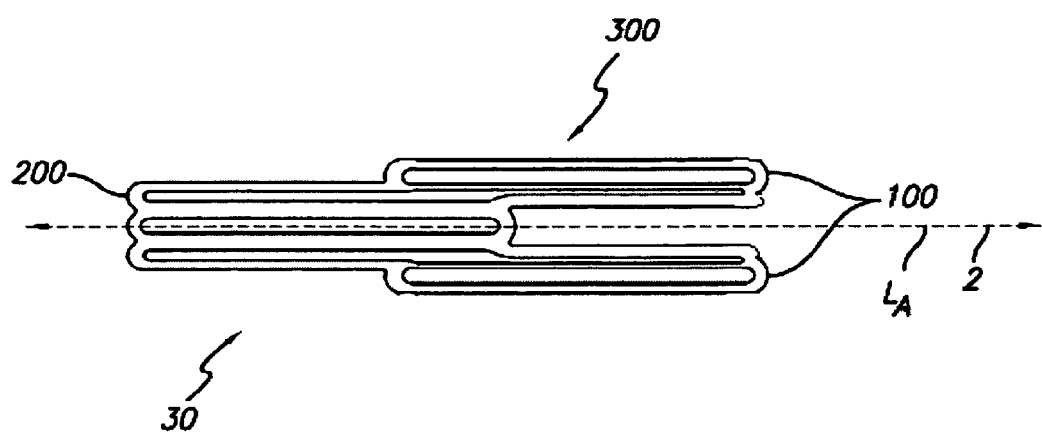
FIG. 1C is a side view of the first implantable frame in the radially compressed state shown in FIG. 1B.

Although the following discussion, along with the figures, describes illustrative embodiments, those skilled in the art will understand that variations and combinations of the described embodiments are also disclosed herein.

The terms "implantable frame" and "frame" are used interchangeably to refer to the structures disclosed herein to one of skill in the art. Preferably, the frames are configured for implantation within a body vessel.

The terms "proximal" and "distal" are used to connote a direction or position relative to each other. Unless otherwise indicated, the recitation of "proximal" or "distal" portions of a frame does not refer to any particular orientation of the implantable frame within a body. The implantable frames described herein can be used in many different body lumens, including both the arterial and venous system, and can be implanted in any suitable orientation within the body.

A frame "perimetrically defining" an opening means that substantially the entire perimeter of the opening is defined by portions of the frame. A frame opening "bounded" by a specified portion of the frame means that at least part of the perimeter of the opening is defined by the specified portion of the frame. For example, an implantable frame can comprise an opening between a substantially cylindrical exterior surface and a substantially cylindrical interior lumen that are bounded by a specified portion of the implantable frame may also be perimetrically defined by a combination of the specified portion of the implantable frame and other portions of the implantable frame.

The term "circumferential" or "circumferentially" refers to a direction or displacement measured along the exterior surface area of an assembled implantable frame in the expanded configuration that is transverse to the longitudinal axis of the implantable frame. The recitation of a first structural feature "circumferentially adjacent" to a second structural feature means that the first structural feature is the nearest first structural feature to the second structural feature when moving circumferentially along the exterior surface of an implantable frame. The term "circumferential distance" means distance measured along the exterior surface of an implantable frame in the expanded configuration.

The term "longitudinal" or "longitudinally" refers to a direction measured along the longitudinal axis of the implantable frame. The term "longitudinally opposite" means positioned in a distal or proximal direction along the exterior surface of an implantable frame parallel to the longitudinal axis of the implantable frame. The recitation of a first structural feature "longitudinally adjacent" to a second structural feature means that the first structural feature is the nearest first structural feature to the second structural feature when moving longitudinally along the exterior surface of an implantable frame. The term "longitudinal distance" means a distance or displacement measured parallel to the longitudinal axis of an implantable frame in the expanded configuration, measured along the exterior surface area of the implantable frame.

The term "arcuate" refers to a curved structure or portion thereof.

The term "semi-circular" refers to an arcuate structure forming a portion of a circle.

The term "symmetrically positioned" refers to a similarity in size, shape, or relative position of corresponding parts.

The term "superelasticity" is used herein to describe the property of certain shape memory alloys to return to their original shape upon unloading after a substantial deformation while in their austenitic state. Superelastic alloys can be readily strained while in their austenitic state with minimal plastic deformation. Alloys that show superelasticity may also undergo a thermoelastic martensitic transformation.

As used herein, the term "strut" refers to a substantially straight portion of a frame, while the term "bend" refers to an arcuate portion of the frame.

As used herein, the terms "peak" and "valley" are used interchangeably to refer to bends in portions of a frame.

The term "symmetrically positioned" refers to a similarity in size, shape, or relative position of corresponding parts.

Typically, implantable frames are subjected to periodic and repeated radial compression and expansion upon implantation. For example, frames implanted in the vascular system are subject to radial movement resulting from periodic blood flow, and accompanying changes in fluid flow rate and pressure due to the approximately 8 million heart beats of a human patient every year. Frames in veins may undergo radial compression as veins dilate or prolapse in response to changes in body activity or position, in addition to pulsatile blood flow. The stress and/or strain experienced along the length of an implantable frame during radial compression or expansion is typically not uniform, and there are areas of relatively low stress and/or strain. Implantable frames comprising sinusoidal hoop members, the radial arcs often experience areas of high mechanical strain and stress during radial compression and expansion, which can lead to fatigue and even failure (e.g., fracture of the frame). One method of predicting the stress and/or strain state in the structure is finite element analysis (FEA), which utilizes finite elements (discrete locations). "Finite element analysis" is a mathematical approach wherein a frame structure is segmented into many pieces that have closed form solutions. That is, each piece can be defined by a linear equation, and hence is a "finite element." Collectively, the linear equations of the pieces form a system of equations that are simultaneously solvable. Computer programs for simulating finite element analysis in various applications exist. For example, design engineers use finite modeling programs. Typically, many thousands of elements are created to model a subject object and in particular three-dimensional objects. For each element, there is geometric information such as an x-y-z coordinate at a point in the element, an element type, material property, stress value, displacement, thermal value, etc. Such information is definable by linear equations for the elements. To that end, finite analysis is employed to model the subject object. Examples of finite modeling programs include: ABAQUS by Hibbitt, Karlsson, and Sorensen, Inc. of Pawtucket, R.I., ANSYS by Swanson Analysis Systems Inc. of Houston, Pa.: SUPERTAB by Structural Dynamics Research corp. of Ohio; and PAT-RAN by PDA Engineering of Costa Mesa, Calif. Typical FEM software comprises modules to create an element mesh from a plurality of device segments (e.g., to create a representation of a simulated device), to analyze a defined problem, and to review results of modified parameters on device design.

Preferred frame configurations were developed that desirably distribute mechanical load (e.g., strain or stress) imposed by periodic radial contraction and expansion. These preferred frame configurations therefore permit the selection of frame configurations with a lower probability of fracture and irritation of the vessel. Preferred frame designs may provide improved and more uniform strain distribution. Certain critical frame regions showed higher strain during FEA analysis. These included the bends of the proximal and distal hoop members as well as the points of attachment of bridging members to either hoop member. In general, strain was largely concentrated in radial arcs, flexural arcs and/or flexural struts. In bend areas where initial stress and/or strain were high, the geometry of the bend was changed to reduce the maximum stress and/or strain in these areas.

Preferred frame configurations may be discussed with reference to certain preferred frame configurations comprising two or more undulating hoop members joined by longitudinal connecting members to form tubular implantable frames, described herein to illustrate various embodiments of the invention. Preferred frame geometries allow radial compression of the frame (crimping) around a conventional delivery balloon catheter, resulting in a low profile (e.g., 6 F) guiding catheter compatible stent delivery system. The percentage of axial shortening upon expanding the balloon is preferably minimized, and can be less than 5%.

In a first embodiment, preferred implantable frames include two hoop members joined by a plurality of longitudinal connecting members. For example, a first implantable frame 12 is provided as shown in FIGS. 1A-2B. The first implantable frame 12 includes a proximal undulating hoop member 100 connected to a distal undulating hoop member 200 by a plurality of longitudinal connecting members 300. Preferably, the undulating hoop members 100, 200 have the same or substantially similar configurations. In the first implantable frame 12, the proximal undulating hoop member 100 is longitudinally adjacent to the distal undulating hoop member 200, but is oriented in the opposite longitudinal direction. Most preferably, the frames assume a radially expanded configuration having a pair of longitudinally adjacent radially compressable undulating hoop members connected by a plurality of substantially parallel longitudinal connecting members, as shown, for example, in the first implantable frame 12. The implantable frame can have a substantially cylindrical exterior surface area defining a plurality of openings therein. The frame openings are preferably defined by at least a portion of the plurality of hoop members, and at least one longitudinal connecting member.

Certain structural features of the implantable frames may be discussed herein with reference to flat plan schematic views, which are two dimensional representations of an implantable frame obtained by theoretically bisecting the implantable frame parallel to its longitudinal axis, "unrolling" the frame and pressing the implantable frame into a flat configuration. FIG. 1A is a flat plan schematic view of the first implantable frame 12. FIG. 1A shows an unrolled flat plan view 10 of the first implantable frame 12. The first implantable frame 10 is oriented along a longitudinal axis L.sub.A, having a proximal direction 2 and distal direction 4.

A flat plan view can be schematically converted into an assembled view of the implantable frame by "rolling" the two transverse edges out of the plane of the flat plan view and joining portions of the transverse edges of the frame to form a three dimensional assembled implantable frame. Reference to the flat plan view 10 is provided to show the configuration of the entire implantable frame 12 in a two-dimensional drawing, but does not, however, suggest or imply any that first implantable frame 12 must be manufactured by any the particular method of manufacture involving the manipulation of a frame from a flat plan to and assembled configuration. Flat plan views are provided merely to illustrate the entire configuration of a frame in a two-dimensional manner, without limiting the manner in which the implantable frames are manufactured. The flat plan view 10 of FIG. 1A can be converted to an "assembled" radially expanded configuration 20 shown in perspective view of FIG. 1B by theoretically "rolling" the frame around the longitudinal axis L.sub.A so as to "connect" portions of the first implantable frame 12 between point A and point B at the proximal edge of the implantable frame 12 and point A' and point B' at the distal end of the implantable frame 12, respectively. The implantable frame 12 may be manufactured in any suitable manner. Preferably, the implantable frame 12 is manufactured without providing the frame 12 in the flat plan view 10. Instead, the implantable frame 12 is preferably produced in the "assembled" configuration 20 by laser cutting away portions of a solid tube of self-expanding material in a radially compressed configuration, and permitting the frame to expand to assume the radially expanded configuration 20 shown in FIG. 1B. Alternatively, a sheet of suitable material can be cut to form a frame in a planar configuration shown in the flat plan view 10 in FIG. 1A, which can be rolled into the assembled configuration of view 20 by joining to itself by any suitable means, as indicated above.

The frame is preferably moveable between a radially compressed state and a radially expanded state by any suitable means within a body vessel, including balloon expansion or self-expansion from a delivery catheter positioned within a body vessel. The first implantable frame 10 is moveable from the expanded state 20 shown in FIG. 1B to a radially compressed state 30 shown in FIG. 1C. The radially compressed configuration 30 is formed by radially compressing the first implantable frame 12 in the assembled configuration 20 in FIG. 1B around the longitudinal axis L.sub.A.

Referring to FIGS. 1A-2B, the first implantable frame 12 comprises a proximal undulating hoop member 100 connected to a distal undulating hoop member 200 by an array of longitudinal connecting members 300, including a first longitudinal connecting member 310 and a second longitudinal connecting member 320 and a third longitudinal connecting member 330. The first implantable frame 12 includes a total of eight longitudinal connecting members 300, with the remaining longitudinal connecting members designated 312a, 312b, 312c, 312d and 312e in FIGS. 1A and 2B. The second longitudinal connecting member 320 is circumferentially adjacent to the first longitudinal connecting member 310 on one side, and longitudinally adjacent to the third longitudinal connecting member 330 on the opposite side. Each longitudinal connecting member preferably extends between a first hoop member 100 and a second hoop member 200. Preferably, the longitudinal connecting members 300 are of substantially the same length and have a substantially constant and substantially identical cross section throughout their entire length. Preferably, the longitudinal connecting members are substantially straight. In the first implantable frame 12, all eight of the longitudinal connecting members 300 are oriented substantially parallel to one another, and are substantially parallel to the longitudinal axis of the implantable frame $L_A$.

Figure 2B:
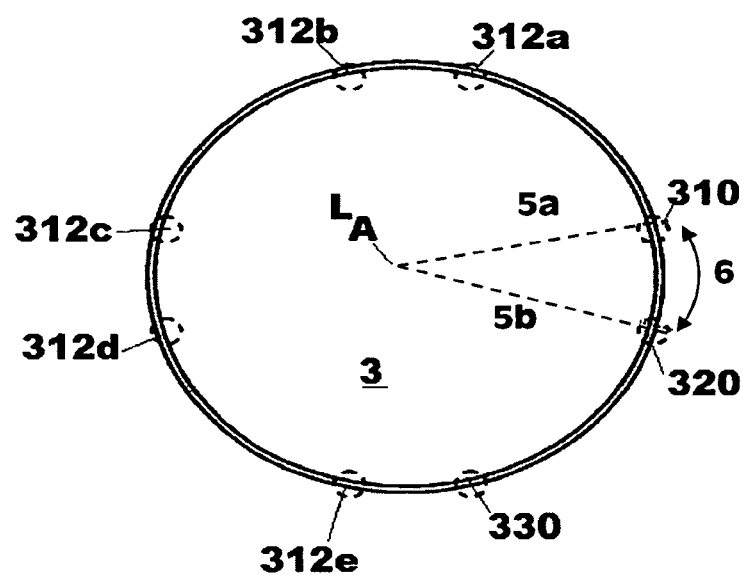
FIG. 2B is a cross sectional view of the expanded first implantable frame of FIG. 1A within the cross sectional plane shown in FIG. 2A.

FIG. 2A shows a hypothetical cross sectional plane 1000 bisecting the perspective view 20 of the first implantable frame 12 shown in FIG. 1B. FIG. 2B shows the cross sectional view of the first implantable frame 12 within the hypothetical cross sectional plane 1000 shown in FIG. 2A, showing the arrangement of longitudinal connecting members 300 around the perimeter of the first implantable frame 12. Preferably, the implantable frame includes one or more pairs of closely-spaced longitudinal connecting members. The recitation of "closely-spaced" as used herein to describe pairs of longitudinal connecting members means that at least one of the pair of longitudinal connecting members is circumferentially closer to the other longitudinal connecting member than to another adjacent longitudinal connecting member. Referring to the first implantable frame 12 illustrated in FIGS. 2A-2B, the first implantable frame includes four pairs of closely spaced longitudinal connecting members: 310-320, 330-312e, 312c-312d and 312a-312b. Each pair of closely-spaced longitudinal connecting members is circumferentially closer to the other closely-spaced longitudinal connecting member than to the other circumferentially adjacent longitudinal connecting member. The second longitudinal connecting member 320 is circumferentially adjacent both the first longitudinal connecting member 310, and the third longitudinal connecting member 330, but is only closely-spaced with respect to the first longitudinal connecting member 310.

The circumferential distance between longitudinally adjacent longitudinal connecting members can be expressed as a radial angle subtended along the perimeter of a cross section of the implantable frame. For example, a first angle 6 is subtended between the closely-spaced circumferentially adjacent longitudinal connecting members 320 and 310, as shown in FIG. 2B. The first radial angle 6 is measured between a first radius 5a extending from the longitudinal axis $L_A$ to the middle of the first longitudinal connecting member 310, and a second radius 5b extending from the longitudinal axis $L_A$ to the middle of the second longitudinal connecting member 320. Preferably, the angle subtended between closely-spaced longitudinal connecting members is a function of the total number of longitudinal connecting members 300 in the implantable frame. The implantable frame may include a first longitudinal connecting member and a closely-spaced second longitudinal connecting member where the angle subtended 6 by a hypothetical arc extending circumferentially between the first longitudinal connecting member and the second longitudinal connecting member is less than $(2\pi/n)$ radians, where n is the number of longitudinal connecting members connecting the longitudinally adjacent hoop members. The integer (n) is preferably greater than or equal to 2, including 2, 3, 4, 5, 6, 7, 8, 9, 10, 11, 12, 13, 14, 15, 16, 17, 18, 19, 20, 21, 22, 23, 24, 25, 26, 27, 28, 29, 30, or more. More preferably, (n) is 4, 5, 6, 7, 8, 9, 10, 11 or 12. Most preferably, (n) is 4, 6 or 8. For example, the first implantable frame 12 includes eight longitudinal connecting members (n=8) and the subtended angle 5 is less than $(2\pi/8)$ radians (i.e., less than 45 degree.). Each of the closely-spaced pairs of longitudinal connecting members in the first implantable frame 12 have an equal angle subtended between each longitudinally-spaced pair that is approximately equal to about $(\pi/8)$ radians (i.e., about 22.5 degree.). Other implantable frame embodiments provide implantable frames with two or more pairs of closely-spaced longitudinal connecting members having different circumferential distances between two or more of the closely-spaced pairs of longitudinal connecting members. For example, an implantable frame may include a first pair of closely-spaced longitudinal connecting members circumferentially placed to subtend a first angle less than $(2\pi/n)$ radians, and a second pair of closely-spaced longitudinal connecting members circumferentially placed to subtend a second angle less than the first angle. Alternatively, an implantable frame may include a first pair of closely-spaced longitudinal connecting members circumferentially placed to subtend a first angle greater than or equal $(2\pi/n)$ radians, and a second pair of closely-spaced longitudinal connecting members circumferentially placed to subtend a second angle less than $(2\pi/n)$ radians.

Preferably, the circumferential distance subtended by the angle δ subtended between the first longitudinal connecting member 310 and the second longitudinal connecting member 320 is less than 25% of the longitudinal length of the longitudinal connecting members 310, 320, and more preferably about 5, 6, 7, 8, 9, 10, 11, 12, 13, 14, 15, 16, 17, 18, 19, 20, 21, 22, 23, 24 or 25% of the length of the longitudinal connecting members 310, 320, and most preferably about 10% to about 15% of the length of the longitudinal connecting members 310, 320.

An implantable frame preferably further includes two or more hoop members axially aligned around a longitudinal axis of the frame. The hoop members can have any suitable configuration. The frame preferably includes one or more undulating hoop members formed from a plurality of interconnected struts and bends oriented along the longitudinal axis of the frame. The first implantable frame 12 comprises a first hoop member 100 axially aligned with respect to a second hoop member 200 and connected by the plurality of longitudinal connecting members 300. Each hoop member 100, 200 is a substantially circular ring comprising an undulating pattern of struts and bends, however hoop members may have any suitable configuration. The first hoop member 100 and the second hoop member 200 have the same size and configuration of struts and bends, but implantable frames may include hoop members having different configurations or sizes. The first hoop member 100 and the second hoop member 200 are substantially equal in radius and are concentrically aligned in the assembled frame configuration. Preferably, each hoop member 100, 200 is formed from a plurality of struts of substantially equal length and cross-sectional area, as shown in the first implantable frame 12, although implantable frames may include struts of different lengths or cross sectional areas. Each hoop member 100, 200 can have any suitable number and combination of struts and bends. For example, a frame can include a first undulating hoop member having a total of (m) struts joined to a total of up to (2 m) longitudinal connecting members, wherein (m) is preferably an integer equal to 2-16, preferably 2-8. Referring to the first implantable frame 12, each hoop member 100, 200 is an undulating hoop member formed from four struts joined to one another by one or more bends, each hoop member 100, 200 having a total of eight bends (m=4). The hoop members 100, 200 of the first implantable frame 12 are joined by a total of eight (n=2 m=8) longitudinal connecting members. Each hoop member typically includes an undulating pattern of struts and bends extending along the axis of the frame. Preferably, the ratio of bends to struts in an undulating hoop member is 1:1 to 3:1, more preferably 2:1 to 3:1, including 1:1.5, 1:2, 1:2.5, 1:3 and any other ratio between 1:1 and 1:3. Undulating hoop members desirably comprise struts having a substantially equal length within each undulating hoop member. Alternatively, one or more hoop members can have a planar rather than undulating geometry, such as a single bent member forming an annular shape. The plurality of hoop members can have the same or different configurations, but are preferably concentrically aligned along the longitudinal axis of the frame. Each of the bends in the hoop members are preferably connected to a longitudinally adjacent hoop member by at least one longitudinal connecting member.

The hoop members 100, 200 preferably define a circumference enclosing a lumen of substantially equal area. Each hoop member 100, 200 desirably forms a perimeter around a substantially circular or elliptical lumen. FIG. 2B shows a cross sectional view of the first implantable frame 12 defining a substantially circular lumen 3 centered on the longitudinal axis $L_A$. The first hoop member 100 is longitudinally adjacent to the second hoop member 200. Longitudinally adjacent hoop members are preferably oriented in a "peak-to-peak" orientation, and can be positioned to align longitudinally adjacent struts circumferentially parallel to one another along the exterior surface of the frame. For example, the first hoop member 100 is oriented in a peak-to-peak orientation with respect to the longitudinally adjacent second hoop member 200.

The hoop members can further comprise a plurality of lateral support arms connecting facing pairs of adjacent struts within the hoop members positioned at the ends of the frame. A lateral support arm is a portion of a frame extending between portions of a single undulating hoop member. Each undulating hoop member 200, 300 of the first implantable frame 12 includes two lateral support arms 110 connecting circumferentially adjacent struts. Each lateral support arm 110 preferably comprises a single bend connecting a pair of lateral support struts. An implantable frame can comprise any suitable number of lateral support arms. Hoop members positioned at the end of a frame preferably comprise one lateral support arm joining circumferentially adjacent struts of each hoop member and extending toward the ends of the frame. Preferably, each lateral support arm bridges a single bend in an undulating hoop member.

Figure 3A:
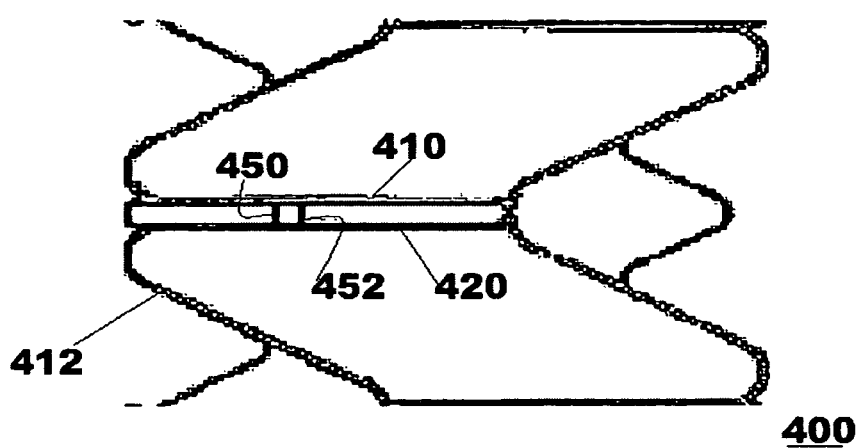
FIG. 3A is a side view of a second implantable frame in the expanded configuration.
Figure 3B:
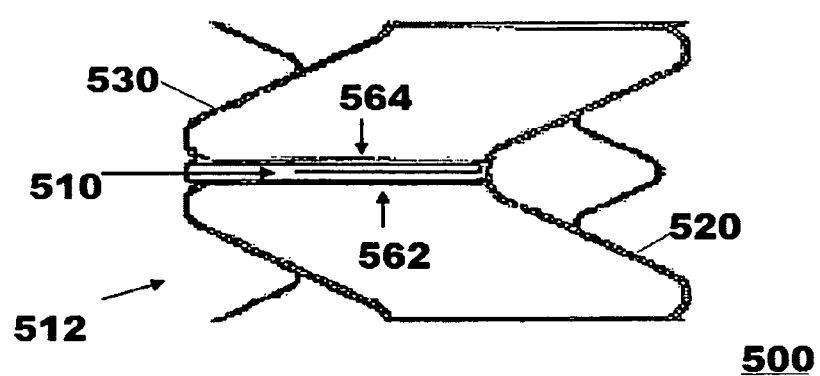
FIG. 3B is a side view of a third implantable frame in the expanded configuration.

The support frame can optionally comprise additional structures between circumferentially adjacent longitudinal connecting members, such as circumferential reinforcing members and longitudinal attachment members. Circumferential reinforcing members extend circumferentially between longitudinal connecting members. An implantable frame can comprise any suitable number of circumferential reinforcing members, longitudinal attachment members, or combination thereof, positioned in any suitable position and orientation with respect to one another. FIG. 3A shows a side view of a second implantable frame 412 in the radially expanded configuration. The second support frame 412 is the same as the first support frame 12 except as described below. The second support frame 412 comprises a first circumferential reinforcing member 450 and a second circumferential reinforcing member 452 extending in parallel to one another between the first longitudinal connecting member 410 and a second longitudinal connecting member 420.

An implantable frame may also comprise longitudinal attachment members positioned between longitudinal connecting members, but attached to only on hoop member. Longitudinal attachment members extend longitudinally from a hoop member at a first end, while remaining unattached to the frame at the opposite end. The longitudinal attachment member can comprise a flexible material suitable for bending into the central lumen of the implantable frame and can include one or more points of attachment for material. For example, a valve leaflet or graft material can be attached to the longitudinal attachment member. FIG. 3C is a side view 500 of a third implantable frame 512, which is identical to the first implantable frame 12 except that the third implantable frame 512 further comprises at least one longitudinal attachment member 510 attached to the first undulating hoop member 520 and extending between a first longitudinal connecting member 562 and a second longitudinal connecting member 564. The longitudinal attachment member 510 is preferably positioned between a pair of closely spaced longitudinal connecting members. The first longitudinal connecting member 562 and the second longitudinal connecting member 564 are closely-spaced with respect to each other, have the same length and are oriented substantially parallel to the longitudinal axis of the third implantable frame 512. The longitudinal attachment member can be adapted to bend into the lumen defined by the implantable frame 512, away from the cylindrical outer surface of the implantable frame and serve as an attachment point for material such as a valve leaflet or graft material.

Figure 4A:
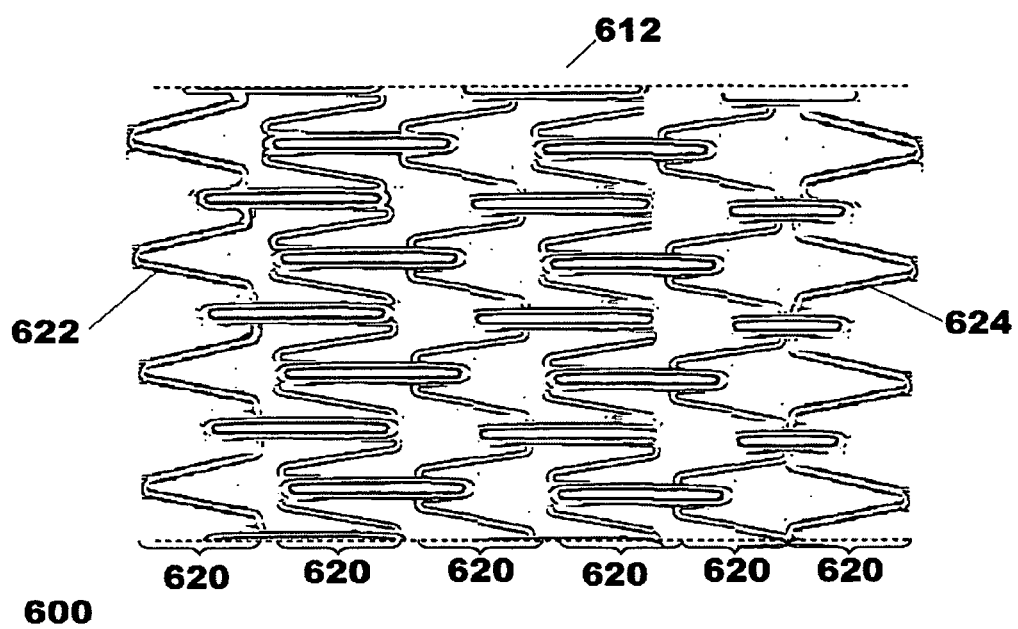
FIG. 4A is an unrolled flat plan view of a fourth implantable frame.

In a second embodiment, implantable frames comprising three or more undulating hoop members are provided. The hoop members can be the same or different. Additional undulating hoop members are preferably longitudinally aligned with a proximal and a distal undulating hoop member by being centered on a common longitudinal axis in the expanded assembled frame configuration. Teachings related to implantable frames comprising one or more undulating hoop members can be applied by one of skill in the art to make and use implantable frames with two, three or more undulating hoop members each preferably joined by one or more longitudinal connecting members. FIG. 4A is a flat plan view 600 of a fourth support frame 612 comprising six axially aligned hoop members 620, including hoop members with different configurations. A distal hoop member 622 and a proximal hoop member 624 each having eight struts and sixteen bends, but oriented in opposite directions. The remaining hoop members positioned between the distal hoop member 622 and the proximal hoop member 624 have one of two different configurations, but all individually comprising eight struts and twenty-four bends. Each hoop member is connected to the longitudinally adjacent hoop member by an array of longitudinal connecting members arranged in pairs of closely-spaced longitudinal connecting members. For example, the distal hoop member 622 is connected to the longitudinally adjacent hoop member by eight longitudinal connecting members.

Figure 4B:
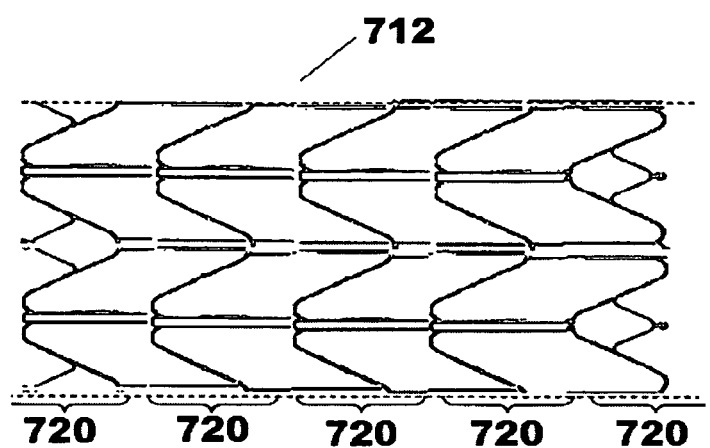
FIG. 4B is an unrolled flat plan view of a fifth implantable frame.

FIG. 4B is a flat plan view 700 of a fifth implantable frame 712 comprising five hoop members 720. Each hoop member 720 includes four struts and eight bends. Each hoop member is connected to the longitudinally adjacent hoop member by an array of longitudinal connecting members arranged in closely-spaced pairs of longitudinal connecting members. The fifth implantable frame may be formed by longitudinally connecting a series of modified undulating hoop members

100, 200 of the first implantable frame 12 in a coaxial manner to define an elongated frame structure. Both the fourth implantable frame 612 and the fifth implantable frame 712 are tubular frames having a pattern of struts and bends defining a plurality of openings in the exterior surface, shown by "rolling" the flat plan views 600 or 700, respectively, to an "assembled" configuration, as described above with respect to the flat plan view 10.

Figure 5:
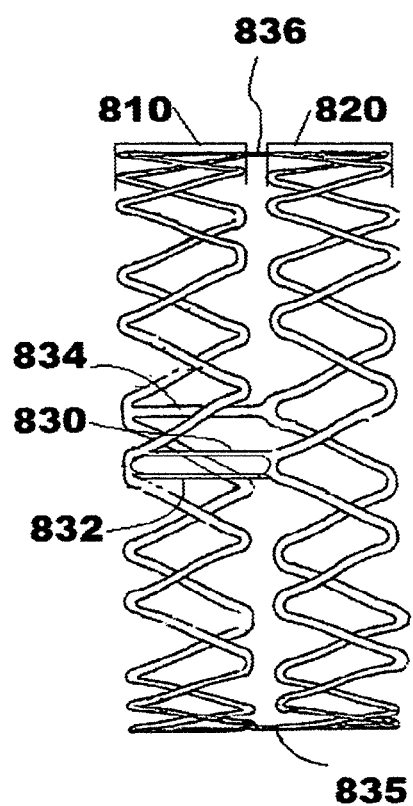
FIG. 5 is a side view of a sixth implantable frame of shown in the radially expanded configuration.

An implantable frame may also include a single pair of closely-spaced longitudinal connecting members. For instance, FIG. 5 shows a side view 800 of a sixth implantable frame 812 formed by joining a first undulating hoop member 810 to a second undulating hoop member 820 by five longitudinal connecting members 830, 832, 834, 835, and 836. A first longitudinal connecting member 830 is closely-spaced with respect to a second longitudinal connecting member 832. The remaining longitudinal connecting members (834, 835, 836) are not closely spaced.

The frame can optionally include a variety of structures or modifications incorporated in or attached to the frame, to secure the frame within a body vessel upon implantation therein. For example, pointed barbs can be attached to or formed in the frame. In one embodiment, barbs can be formed in or joined to one or more bends in undulating hoop members. Other structures or structural modifications for anchoring the frame in a body vessel are known in the art, and include without limitation, forming portions of the frame with barbs, perforations, bioadhesives, roughened surfaces, or heating the frame or portions thereof to bond the frame to the body vessel wall.

The frame can have any size suitable for intralumenal implantation. The length of the frame measured along the longitudinal axis is preferably from up to 50 mm, or preferably between 5 mm and 50 mm or higher, including 5, 6, 7, 8, 9, 10, 11, 12, 13, 14, 15, 16, 17, 18, 19, 20, 21, 22, 23, 24, 25, 26, 27, 28, 29, 30, 30, 32, 34, 35, 36, 38, 40, 42, 44, 45, 46, 48 and 50 mm, and any increment of 0.25 mm or 0.10 mm increment thereof. Some preferred embodiments have lengths of 8, 12, 13, 16, 20, 23, 24, 25, 28, 32 or 33 mm.

The diameter of the expanded configuration of the implantable frame can be selected by one skilled in the art given the desired location for implantation. When in the compressed state for delivery to a desired location within a body lumen, an implantable frame is typically reduced from about two to about six times the diameter of the stents when in their expanded configuration before compression. For example, typical implantable frames may have a compressed external diameter of about 1 millimeter to about 3 millimeters for delivery and an expanded external diameter in a body lumen of about 3 millimeters to about 20 millimeters when released from compression in a large body vessel. Some implantable frames used in veins may have a compressed external diameter of about 1.00, 1.20, 1.25, 1.40, 1.50, 1.60, 1.75, 1.80, 2.00, 2.20, 2.25, 2.30, 2.40, 2.50, 2.60, 2.75, 2.80, 2.90, 3.00 mm or more and an expanded external diameter of up to about 20 mm, including between about 1 and 20 mm. Some implantable frames, for example for arterial body vessels, preferably have external diameters of 2.00, 2.20, 2.25, 2.30, 2.40, 2.50, 2.60, 2.70, 2.75, 2.80, 2.90, 3.00, 3.10, 3.20, 3.25, 3.30, 3.40, 3.50, 3.60, 3.70, 3.75, 3.80, 3.90, 4.00, 4.20, 4.25, 4.30, 4.40, 4.50, 4.60, 4.70, 4.75, 4.80, 4.90, 5.00 mm, or increments of 0.25, 0.10, 0.05 or 0.01 mm between these diameters. Other preferred embodiments, for example for implantation in veins, have expanded external diameters of between about 3 to about 25 mm, including external diameters of 3, 4, 5, 6, 7, 8, 9, 10, 11, 12, 13, 14, 15, 16, 17, 18, 19, 20, 21, 22, 23, 24, 25 mm, or any increments of 0.25, 0.10, 0.05 or 0.01 mm between these diameters. In certain preferred embodiments, the implantable frame has an expanded inner diameter of 1.25, 2.00, 2.50, 2.75, 3.00, or 3.50 mm.

The cross sectional shape of the implantable frame members (including struts, bends and longitudinal connecting members) can be selected by one skilled in the art for particular applications, and can have the same or different shapes throughout the implantable frame or portions thereof. Suitable cross sectional dimensions of an implantable frame or portion thereof can be selected based on a variety of factors, including the intended use of the device, the material and design of the device, and other relevant concerns. The frame forming the undulating hoops, longitudinal connecting struts, or bridging members can have the same or different cross sectional shape(s). In one embodiment, the implantable frame has a square, trapezoidal, circular, triangular or rectangular cross sectional shape. Preferably, the undulating hoop members and the longitudinal connecting struts both have similar cross sectional dimensions. Suitable dimensions for each side of a square or rectangular cross section, or for the diameter of a circular cross section, range from 0.001-inch (0.0254 mm) to about 0.100-inch (2.54 mm). Preferably, the longest cross sectional dimension of an implantable frame member is between about 0.001-inch (0.0254 mm) and 0.0049-inch (0.1245 mm). In one embodiment, one side of a rectangular or square cross sectional area (or diameter of a circular cross sectional area) is between about 0.004-inch (0.102 mm) and about 0.010-inch (0.254 mm). In some embodiments, at least a portion of the frame has a strut thickness of 0.0022, 0.0025, 0.0027, 0.0036, 0.0037, 0.0049, 0.005, 0.0055, 0.006, or 0.009-inch. For example, one preferred embodiment has an implantable frame with a width of 0.2286 mm (0.0090-inch) along the external surface of the implantable frame along the undulating hoop members and the longitudinal connecting members. In some embodiments, the implantable frame can comprise bridging members with a width of about 0.0060-inch or 0.0090-inch. In one preferred embodiment, the implantable frame has a length of 25.00 mm and an external outer diameter of 12.50 mm in the expanded configuration, and an outer diameter of 3.0 mm in the compressed delivery configuration.

Preferred materials for frames include those materials that can provide the desired functional characteristics with respect to mechanical load bearing, biological compatibility, modulus of elasticity, radio-opacity, or other desired properties. For some embodiments, the materials used to form the implantable frames can comprise a material that exhibits excellent corrosion resistance. For some embodiments, the material can be selected to be sufficiently radiopaque and create minimal artifacts during magnetic resonance imaging techniques (MRI). In some embodiments, the implantable frame can comprise a metal, a metal alloy, a polymer, or any suitable combination thereof, for example as frame with multiple layers.

Preferably, the implantable frames are self-expanding stents comprising a material capable of significant recoverable strain to assume a low profile for delivery to a desired location within a body lumen. After release of the compressed self-expanding stent, it is preferred that the frame be capable of radially expanding back to its original diameter or close to its original diameter. Accordingly, some embodiments provide frames made from material with a low yield stress (to make the frame deformable at manageable balloon pressures), high elastic modulus (for minimal recoil), and is work hardened through expansion for high strength. Particularly preferred materials for self-expanding implantable frames are shape memory alloys that exhibit superelastic behavior, i.e., are capable of significant distortion without plastic deformation. Frames manufactured of such materials may be significantly compressed without permanent plastic deformation, i.e., they are compressed such that the maximum strain level in the stent is below the recoverable strain limit of the material. Discussions relating to nickel titanium alloys and other alloys that exhibit behaviors suitable for frames can be found in, e.g., U.S. Pat. No. 5,597,378 (Jervis) and WO 95/31945 (Burmeister et al.). A preferred shape memory alloy is Ni—Ti, although any of the other known shape memory alloys may be used as well. Such other alloys include: Au—Cd, Cu—Zn, In—Ti, Cu—Zn—Al, Ti—Nb, Au—Cu—Zn, Cu—Zn—Sn, CuZn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. These alloys may also be doped with small amounts of other elements for various property modifications as may be desired and as is known in the art. Nickel titanium alloys suitable for use in manufacturing implantable frames can be obtained from, e.g., Memory Corp., Brookfield, Conn. One suitable material possessing desirable characteristics for self-expansion is Nitinol, a Nickel-Titanium alloy that can recover elastic deformations of up to 10 percent. This unusually large elastic range is commonly known as superelasticity.

In some embodiments, the implantable frames are designed to be expanded by a balloon or some other device (i.e., the frames are not self-expanding), and may be manufactured from an inert, biocompatible material with high corrosion resistance that can be plastically deformed at low-moderate stress levels, such as tantalum. The implantable frames can be deployed by both assisted (mechanical) expansion, i.e. balloon expansion, and self-expansion means. In embodiments where the implantable frame is deployed by mechanical (balloon) expansion, the implantable frame is made from materials that can be plastically deformed through the expansion of a mechanical assist device, such as by the inflation of a catheter based balloon. When the balloon is deflated, the frame can remain substantially in the expanded shape. Other acceptable materials include stainless steel, titanium ASTM F63-83 Grade 1, niobium or high carat gold K 19-22. One widely used material for balloon expandable structures is stainless steel, particularly 316L stainless steel. This material is particularly corrosion resistant with a low carbon content and additions of molybdenum and niobium. Fully annealed, stainless steel is easily deformable. Alternative materials for mechanically expandable structural frames that maintain similar characteristics to stainless steel include tantalum, platinum alloys, niobium alloys, and cobalt alloys.

In addition, the frames may be formed from or coated with other materials, such as polymers and bioabsorbable polymers may be used for the implantable frames. In one embodiment, the implantable frame is formed from 316L stainless steel. In another embodiment, the implantable frame is formed from a cobalt chromium alloy. The implantable frames can also comprise (that is, be formed from or coated with) a variety of polymers with limited bioabsorbability, including polyethylene (PE); polypropylene (PP); polyisobutylene; poly(alpha olefin); alkyl (alkyl)acrylates such as poly (n-butyl methacrylate) (PBMA) poly(methyl acrylate) or poly(methyl methacrylate) (PMMA); poly(ethyl acrylate); parylenes such as parylene C; ethyl vinyl acetate (EVA); poly(ethylene-co-vinyl acetate) (PEVA), or copolymers or mixtures thereof.

For some embodiments, it is desirable to provide implantable frames comprising bioabsorbable polymers. Bioabsorbable materials absorb into the body after a period of time. The period of time for the structural frame to absorb may vary, but is typically sufficient to allow desired biological processes such tissue growth to occur at the implant location. The implantable frames can comprise one or more bioabsorbable materials. A wide variety of bioabsorbable materials are known in the art, as well as equivalents thereof, can be used to form implantable frame. Nonlimiting examples of bioabsorbable polymers include polyesters such as poly(hydroxyalkanoates), poly(lactic acid) or polylactide (PLA), poly(glycolic acid) or polyglycolide (PGA), poly(caprolactone), poly (valerolactone) and co-polymers thereof; polycarbonates; polyoxaesters such as poly(ethylene oxalate), poly(alkylene oxalates); polyanhydrides; poly(amino acids); polyphosphazenes; phosphorylcholine; phosphatidylcholine; various hydrogels; polydioxanone, poly(DTE carbonate), and co-polymers or mixtures of two or more polymers. The implantable frames can also include various natural polymers such as fibrin, collagens, extracellular matrix (ECM) materials, dextrans, polysaccharides and hyaluronic acid.

The implantable frames or portions thereof can optionally comprise material that permits identification of the position or orientation of the frame within a body passage. Radiopaque markers are advantageously positioned at one or more ends of the implantable frame to aid the physician in positioning the frame at a site inside a body vessel. For example, portions of the implantable frame can include a radiopaque material that can be identified by X-rays. The frame can also comprise materials that are useful with contrast dyes to identify the frame within a body passage. For example, the first implantable frame 12, as shown in FIG. 1A, comprises a plurality of radiopaque markers 112 attached to the bridging members 110. Numerous materials known in the art, and equivalents thereof, can be used in the implantable frames to provide information about the frame in a body vessel. U.S. Pat. No. 6,409,752, issued Jun. 25, 2002 to Boatman et al., incorporated herein by reference, discloses various radiopaque materials that can be used in or on the implantable frames. Nonlimiting examples of radiopaque materials include, but are not limited to, high-density metals such as platinum, iridium, gold, silver, tantalum or their alloys, or radiopaque polymeric compounds. Preferably, radiopaque materials are highly visible under fluoroscopic illumenation and are visible even at minimal thickness. In some preferred embodiments, the implantable frames comprise radiopaque material such as gold, platinum, tungsten, or iridium, as well as mixtures and alloys thereof, in an eyelet structure attached to one or more bridging members.

The disclosure of various materials for forming the structural frame should not be construed as limiting the scope of the invention. One of ordinary skill in the art would understand that other materials possessing similar characteristics may also be used in the construction of the implantable frame.

The implantable frames may be fabricated using any suitable method known in the art. Preferably, the complete frame structure is cut from a solid tube or sheet of material, and thus the frame would be considered a monolithic unit. Laser cutting, water-jet cutting and photochemical etching are all methods that can be employed to form the structural frame from sheet and tube stock. Still other methods for fabricating the complete frame structure as previously disclosed would be understood by one of skill in the art.

Alternatively, the frame can also be formed from wire using wire forming techniques, such as coiling, braiding, or knitting. By welding the wire at specific locations a closed-cell structure may be created. This allows for continuous production, i.e. the components of the implantable frame may be cut to length from a long wire mesh tube. In addition, an implantable frame is constructed from sheet, wire (round or flat) or tubing. The method of fabrication can be selected by one skilled in the art depending on the raw material used. Techniques for forming implantable frames are discussed, for example, in Dougal et al., "Stent Design: Implications for Restenosis," Rev. Cardiovasc Med. 3 (suppl. 5), S16-S22 (2002), which is incorporated herein by reference in its entirety.

In some embodiments, connections between the strut members and the bends in an undulating hoop member, as well as the connection between the undulating hoop member and the longitudinal connecting members, may be by welding or other suitable connecting means. Other connection means include the use of a binder, heat, or chemical bond, and/or attachment by mechanical means, such as pressing, welding or suturing. In addition, portions of the frame may be attached by applying a bonding coating.

An implantable frame can optionally be sterilized using any suitable technique known in the art, or equivalents thereto. For example, an implantable frame can be sterilized using ethylene oxide sterilization, as described in AAM/ISO 11135:1994 "Medical Devices—Validation and Routine Control of Ethylene Oxide Sterilization," incorporated herein by reference in its entirety. In some embodiments, a sterilized implantable frame satisfies a minimum Sterility Assurance Level (SAL) of about $10^{-6}$.

Vascular prostheses such as stent and stent/grafts undergo a number of different strain conditions in-vivo including: radial strain resulting from the applied diastolic and diastolic blood pressure, bending due to heart/limb movement and radial point loading due to limb motion or impact.

A variety of techniques can be used to measure and control the radial strains applied to vascular prostheses in bench-top simulators. A first technique involves applying a known volumetric fluid displacement to a vascular prosthesis that has been installed in a mock artery of known radial compliance. The volumetric displacement can be adjusted until the applied pressure closely simulates diastolic and diastolic conditions. The resulting radial strain can then be calculated as known in the art, for example with a formula that uses the volumetric displacement and mock artery dimensions. A second technique involves measuring the radial strain of the outside diameter of the mock artery using a laser micrometer. The internal radial strain can then be determined by multiplying the outside strain by a ratio that has been calculated using the outside and inside diameters and poison ratio of the mock artery material.

The implantable frames can be tested by placing them inside latex tubes filled with a phosphate buffered saline (PBS) solution and pulsating the tube volume to simulate physiological vessel compliance conditions (typically 3-5%). The tubes deflect radially with the applied pulsatile pressure. The tube-stent assembly acts as a mechanical system, producing strain levels comparable to the vessel-stent system of the human body. A laser transducer can be used to measure the tube dilation in real-time; Win test uses the resulting signal to control the dilation within preset levels. At various intervals during the durability test, the devices can be removed and examined for mechanical integrity under a scanning electron microscope or with an endoscope assembly. A list of potential failure modes and potential tests that were identified by the MMI/ISO TG150, SC2, WG31 committee in developing their working document for endovascular devices, incorporated herein by reference.

For intravascular applications, the use of x-ray angiography, pressure catheters, or intravascular ultrasound provides a good means for determining the radial dilation and pressures that occur during each heartbeat or extraneous movement. Combining measured data with finite element modeling provides a better understanding of the test parameters that must be generated.

A variety of other test protocols can also be used. Information provided on the FDA Web site about previously approved devices can be useful in developing test protocols. Published papers and articles about applied loading in relevant publications, for example in the orthopedic and intravascular fields. For example, Conti et al., Biomed Sci Instrum 35:339-46 (1999), incorporated herein by reference, discusses testing of intravascular implantable frames.

Optionally, the support frame can include one or more bioactive materials. Preferably, the bioactive material is releasibly associated with the frame, meaning that the bioactive material can be released from a medical device comprising the frame upon implantation. Releasibly associated bioactive materials can be attached to the medical device in any suitable manner, including incorporation of the bioactive material within the frame material, attachment of the bioactive material to the frame material or incorporation of the bioactive material in one or more coatings applied to the frame material.

The bioactive material can be selected to treat indications such as thrombosis, coronary artery angioplasty, renal artery angioplasty, carotid artery surgery, renal dialysis fistulae stenosis, or vascular graft stenosis. The bioactive agent can be selected to perform one or more desired biological functions. An anti-angiogenic or antineoplastic bioactive such as paclitaxel, sirolimus or a rapamycin analog, or a metalloproteinase inhibitor such as batimastaat can be incorporated in or coated on the frame to mitigate or prevent undesired conditions in the vessel wall, such as restenosis. Many other types of bioactive agents can be incorporated in or coated on a support frame.

Medical devices comprising an antithrombogenic bioactive material are particularly preferred for implantation in areas of the body that contact blood. An antithrombogenic bioactive material is any bioactive material that inhibits or prevents thrombus formation within a body vessel. The medical device can comprise any suitable antithrombogenic bioactive material. Types of antithrombotic bioactive materials include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive materials inhibit the adhesion, activation, and aggregation of platelets, which are key components of thrombi and play an important role in thrombosis. Fibrinolytic bioactive materials enhance the fibrinolytic cascade or otherwise aid is dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFT) inhibitors, and other enzymes which cleave fibrin. Further examples of antithrombotic bioactive materials include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, Cl-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive materials such as endothelial progenitor cells or endothelial cells.

Bioactive materials for use in bio-compatible coatings include those suitable for coating on an implantable medical device. The bioactive agent can include, for example, one or more of the following: antiproliferative agents (sirolimus, paclitaxel, actinomycin D, cyclosporin), immunomodulating drugs (tacrolimus, dexamedthasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-.beta.

A bioactive material can be one or more pro-healing therapeutic agents, which include materials that provide or promote endothelial cell seeding. For instance, coatings comprise antibodies to CD34 receptors on progenitor circulating endothelial cells. Nitric oxide, vascular endothelial growth factor, and 17-.beta.-estradiol are other examples of prohealing therapeutic agents. Another prohealing bioactive agent is vascular endothelial growth factor (VEGF). VEGF is an endothelial cell-specific mitogen, and a cytokine involved in processes essential to the growth, maintenance and repair of vascular structures. VEGF can be coated on an implantable frame. Local drug delivery of VEGF from a medical device, such as a stent frame, can reduce in-stent restenosis. Other examples of pro-healing therapeutic agents, along with methods for coating the same on implantable medical devices, are provided in published U.S. Patent Application Nos. 2005/0092440 (filed Nov. 8, 2002, by Weinstein); 2005/0191333 (filed Apr. 28, 2005 by Hsu); and 2005/0148585 (filed Aug. 26, 2004 by Davies et al.), which are incorporated herein by reference.

Various other bioactive materials can be incorporated on or in the frame, including one or more of the following: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as (GP) II b/IIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6.alpha.-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat) and protease inhibitors. Other examples of bioactive coating compounds include antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat. Still other bioactive agents that can be incorporated in or coated on a frame include a PPAR agonist and RXR agonists, as disclosed in published U.S. Patent Application US2004/0073297 to Rohde et al., published on Apr. 15, 2004 and incorporated in its entirety herein by reference.

The device can be coated with polysaccharides, for example as disclosed in published U.S. Patent Application US2004/091605 to Bayer et al., published on May 13, 2004 and incorporated herein by reference in its entirety. In one embodiment, the frame comprises a polysaccharide layer which has improved adhesion capacity on the substrate surface of the frame. For example, the coated frame can comprise the covalent bonding of a non-crosslinked hyaluronic acid to a substrate surface of the frame with the formation of hyaluronic acid layer and crosslinking of the hyaluronic acid layer.

The bioactive materials can be attached to the medical device in any suitable manner. For example, a bioactive can be attached to the surface of the medical device, or be positioned within the frame in pores. One or more bioactives can be coated on or incorporated within a frame. In one embodiment, a frame can be configured to absorb a solution of a bioactive material. For instance, a frame with absorbent properties can be selected, or a portion of a medical device can be coated with a cross-linked polymer hydrogel material to retain a bioactive material for elution within a body vessel. A bioactive can be incorporated by soaking the absorbent portion of the medical device in a solution of the bioactive material and allowing the absorption of the bioactive solution. Subsequently, the solvent can be evaporated to leave the bioactive within the medical device.

In another embodiment, a frame can also be coated with or formed from a biodegradable polymers, as well as copolymers of degradable polymers. A bioactive material can be mixed with or copolymerized with the bioabsorbable polymer. Alternatively, the bioactive material or a mixture of bioactive material and biostable or bioabsorbable polymer can be coated with a second layer comprising a bioabsorbable polymer. Upon implantation, absorption of the bioabsorbable polymer releases the bioactive. Bioabsorbable polymers can be formed by copolymerization of compatible monomers or by linking or copolymerization of functionalized chains with other functionalized chains or with monomers. Examples include crosslinked phosphorylcholine-vinylalkylether copolymer and PC-Batimastat copolymers. In one embodiment, the frame is coated with a coating of between about 1 .mu.m and 50 .mu.m, or preferably between 3 .mu.m and 30 .mu.m, although any suitable thickness can be selected. The coating can comprise a bioactive material layer contacting a separate layer comprising a carrier, a bioactive material mixed with one or more carriers, or any combination thereof. The carrier can be biologically or chemically passive or active, but is preferably selected and configured to provide a desired rate of release of the bioactive material. In one embodiment, the carrier is a bioabsorbable material, and one preferred carrier is poly-L-lactic acid. U.S. patent application Ser. No. 10/639,225, filed Aug. 11, 2003 and published as US2004/0034409A1 on Feb. 19, 2004, describes methods of coating a bioabsorbable metal support frame with bioabsorbable materials such as poly-L-lactic acid that are incorporated herein by reference.

Implantable frames or prostheses comprising the implantable frame can be delivered into a body lumen using a system which includes a catheter. In some embodiments, implantable frames can be intralumenally delivered inside the body by a catheter that supports the implantable frame in a compacted form as it is transported to the desired site, for example within a body vessel. Upon reaching the site, the implantable frame can be expanded and securably placed within the body vessel, for example by securably engaging the walls of the body vessel lumen. The expansion mechanism may involve forcing the stent to expand radially outward, for example, by inflation of a balloon formed in the distal portion of the catheter, to inelastically deform the stent and fix it at a predetermined expanded position in contact with the lumen wall. The expansion balloon can then be deflated and the catheter removed. In another technique, the implantable frame is formed of an elastic material that will self-expand after being compacted. During introduction into the body, the implantable frame is restrained in the compacted condition. When the stent has been delivered to the desired site for implantation, the restraint is removed, allowing the implantable frame to self-expand by its own internal elastic restoring force. Once the implantable frame is located at the constricted portion of the lumen, the sheath is removed to expose the stent, which is expanded so it contacts the lumen wall. The catheter is subsequently removed from the body by pulling it in the proximal direction, through the larger lumen diameter created by the expanded prosthesis, which is left in the body.

In some embodiments, the implantable frames impart radially outward directed force during deployment, whether self-expanding or radially-expandable. The radially outward directed force can serve to hold the body lumen open against a force directed radially inward, as well as preventing restriction of the passageway through the lumen by intimal flaps or dissections generated by, such as prior balloon angioplasty. Another function of the radially outward directed force can also fix the position of the stent within the body lumen by intimate contact between the stent and the walls of the lumen. Preferably, the outwardly directed forces does not traumatize the lumen walls.

Figure 6:
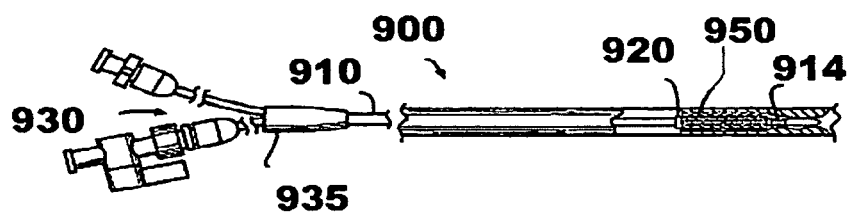
FIG. 6 is a schematic view of a delivery system showing portions of a delivery catheter and an implantable frame expanding from the compressed state to the expanded state.

The implantable frames may be delivered, for example, on their own or as part of an implantable prosthetic valve. FIG. 6 illustrates a delivery system 900. The delivery system 900 includes a catheter 910 having a distal end 914. A balloon 920 is positioned on the distal end 914 of the catheter 910. A connector assembly 930 is disposed at the proximal end 935 of the catheter 910 and is adapted to facilitate expansion of the balloon 920 as is known in the art. The connector assembly 930 provides access to an interior lumen of the catheter 910 to provide access to the balloon 920, and possibly a guidewire (not illustrated) or other conventional component. A balloon expandable implantable frame 950 is disposed on the distal end 914 of the catheter 910. The implantable frame 950 surrounds the balloon 620 and is initially, prior to placement in a body vessel, in its unexpanded state. This positioning allows the balloon 920, upon inflation, to expand the implantable frame 950 into its expanded state. The implantable frame 950 can be configured to providing artificial support to a body vessel or can form part of a valve or stent graft. The implantable frame 950 can be selected from the group consisting of: the first implantable frame 12, the second implantable frame 412, the third implantable frame 512, the fourth implantable frame 612, the fifth implantable frame 712 and the sixth implantable frame 812, as described above.

Delivery of the implantable frame 950 can be performed by inserting the distal end 914 of the catheter 910 into a body vessel and navigating the distal end 914, and the surrounding implantable frame 950, to a point in a vessel in need of artificial support. The catheter 910 can be placed over a guidewire (not illustrated) to facilitate navigation. Once the implantable frame 950 is at the point of treatment, the balloon 920 can be inflated in the conventional manner. Inflation of the balloon 920 forces the implantable frame 950 to expand. During expansion, in which the implantable frame 950 changes from its compressed state to its expanded state, circumferentially adjacent longitudinal connecting members can deviate from the axially-displaced configuration associated with the unexpanded state of the implantable frame 950, becoming substantially aligned in the axial direction. Following expansion, the balloon 920 can be deflated. The catheter 910 can then be withdrawn from the vessel, leaving the implantable frame 950 in its expanded state at the point of treatment within the body vessel.

An appropriately sized delivery catheter can be selected by one skilled in the art for a given application. For example, some embodiments can be delivered using a delivery catheter selected from one or more delivery catheter sizes from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 french (F) delivery catheters, or increments of 0.1 F therebetween. In some embodiments, a delivery catheter sized between 1 and 25 F, or preferably between about 1.5 F and 5 F can be used, preferably a 1.8 F (0.60 mm), 2.0 F (0.66 mm), 2.3 F (0.75 mm), 2.6 F (0.85 mm), 2.7 F (0.9 mm), 2.9 F (0.95 mm), or 3.3 (1.10 mm) delivery catheters. Kits comprising implantable frames are also provided. In one embodiment, a kit comprises an implantable frame and a delivery catheter.

The implantable frames can be placed in any medically appropriate location for a given application. For example, in some embodiments, the implantable frame can serve as part of a venous valve prosthetic and be implanted in the femoral vein, including at the proximal (groin), mid (mid section) or distal (adjacent to the knee) portions of the vein. Implantable frames can be deployed at various locations and lumens in the body, such as, for example, coronary, vascular, nonvascular and peripheral vessels, ducts, and the like, including but not limited to cardiac valves, venous valves, valves in the esophagus and at the stomach, valves in the ureter and/or the vesica, valves in the biliary passages, valves in the lymphatic system and valves in the intestines. In one embodiment, a valve leaflet is attached to the frame to provide an implantable valve prosthesis that can be implanted within a vein, for instance, near an incompetent venous valve to treat venous valve insufficiency. Methods of treatment preferably include the steps of loading an implantable frame, or a device comprising an implantable frame, in a compressed state into a delivery catheter, inserting the delivery catheter into a body vessel, translating the delivery catheter to a desired location, deploying the device comprising the implantable frame by securably placing the device in an expanded state at the desired location, and withdrawing the delivery catheter from the body vessel.

The foregoing disclosure includes the best mode devised by the inventor for practicing the invention. It is apparent, however, that several variations in intralumenal graft assemblies in accordance with the present invention may be conceivable by one skilled in the art. Inasmuch as the foregoing disclosure is intended to enable one skilled in the pertinent art to practice the instant invention, it should not be construed to be limited thereby, but should be construed to include such aforementioned variations.

We claim:

1. An implantable frame defining a lumen extending between a proximal end and a distal end along a longitudinal axis, the implantable frame moveable between a compressed state and an expanded state and comprising:
   a proximal hoop member;
   a distal hoop member;
   each hoop member comprising a plurality of interconnected struts and bends arranged in an undulating shape;
   a closely-spaced pair of longitudinal connecting members connecting the proximal hoop member to the distal hoop member, the closely-spaced pair of longitudinal connecting members comprising a first longitudinal connecting member and a second longitudinal connecting member; and
   a structural member extending from the first longitudinal connecting member to the second longitudinal connecting member.

2. The implantable frame of claim 1, wherein the structural member comprises a circumferential reinforcing member.

3. The implantable frame of claim 1, further comprising a second structural member extending from the first longitudinal connecting member to the second longitudinal connecting member.

4. The implantable frame of claim 3, wherein the second structural member comprises a circumferential reinforcing member.

5. The implantable frame of claim 3, wherein each of the first and second structural members comprises a circumferential reinforcing member.

6. The implantable frame of claim 5, wherein the circumferential reinforcing members are parallel to each other.

7. The implantable frame of claim 1, further comprising a longitudinal attachment member disposed between the first and second longitudinal connecting members.

8. The implantable frame of claim 1, wherein the first closely-spaced pair of longitudinal connecting members extends from a first bend of a first hoop member toward a first bend of a second hoop member.

9. The implantable frame of claim 1, further comprising a radiopaque marker.

10. The implantable frame of claim 9, wherein the radiopaque marker is attached to a bridging member extending between first and second struts of a hoop member.

11. The implantable frame of claim 1, wherein the implantable frame is self-expandable.

12. The implantable frame of claim 1, wherein the implantable frame requires mechanical expansion to move from the compressed state to the expanded state.

13. The implantable frame of claim 1, wherein the implantable frame comprises stainless steel.

14. The implantable frame of claim 1, wherein the implantable frame comprises a shape memory alloy.

15. The implantable frame of claim 14, wherein the shape memory alloy comprises a Nickel-Titanium alloy.

16. The implantable frame of claim 1, wherein the implantable frame comprises a polymer.

17. The implantable frame of claim 1, wherein the implantable frame comprises a bioabsorbable polymer.

18. The implantable frame of claim 1, wherein the implantable frame includes a bioactive agent.

19. An implantable frame defining a lumen extending between a proximal end and a distal end along a longitudinal axis, the implantable frame moveable between a compressed state and an expanded state and comprising:
   a proximal hoop member;
   a distal hoop member;
   each hoop member comprising a plurality of interconnected struts and bends arranged in an undulating shape;
   a closely-spaced pair of longitudinal connecting members connecting the proximal hoop member to the distal hoop member, the closely-spaced pair of longitudinal connecting members comprising a first longitudinal connecting member and a second longitudinal connecting member;
   a first structural member extending from the first longitudinal connecting member to the second longitudinal connecting member; and
   a second structural member extending from the first longitudinal connecting member to the second longitudinal connecting member;
   wherein the implantable frame is self-expandable.

20. An implantable frame defining a lumen extending between a proximal end and a distal end along a longitudinal axis, the implantable frame moveable between a compressed state and an expanded state and comprising:
   a proximal hoop member;
   a distal hoop member;
   each hoop member comprising a plurality of interconnected struts and bends arranged in an undulating shape;
   a closely-spaced pair of longitudinal connecting members connecting the proximal hoop member to the distal hoop member, the closely-spaced pair of longitudinal connecting members comprising a first longitudinal connecting member and a second longitudinal connecting member;
   a first circumferential reinforcing member extending from the first longitudinal connecting member to the second longitudinal connecting member; and
   a second circumferential reinforcing member extending from the first longitudinal connecting member to the second longitudinal connecting member;
   wherein the circumferential reinforcing members are parallel to each other; and
   wherein the implantable frame is self-expandable.

* * * * *